(12) United States Patent
Ciok et al.

(10) Patent No.: US 6,849,066 B1
(45) Date of Patent: Feb. 1, 2005

(54) COLLECTING BAG HAVING AN ACCOMMODATING MEANS FOR A CLOSURE DEVICE

(75) Inventors: Danuta Ciok, Nivå (DK); Martin von Bulow, Helsingør (DK)

(73) Assignee: Coloplast A/S, Humlebaek (DK)

( * ) Notice: Subject to any disclaimer, the term of this patent is extended or adjusted under 35 U.S.C. 154(b) by 18 days.

(21) Appl. No.: 10/070,422

(22) PCT Filed: Sep. 1, 2000

(86) PCT No.: PCT/DK00/00478

§ 371 (c)(1),
(2), (4) Date: Mar. 18, 2002

(87) PCT Pub. No.: WO01/21115

PCT Pub. Date: Mar. 29, 2001

(30) Foreign Application Priority Data

Sep. 17, 1999 (DK) ........................................ 1999 01319

(51) Int. Cl.[7] ................................................. A61F 5/44
(52) U.S. Cl. ........................ 604/332; 604/328; 604/335
(58) Field of Search .......................... 604/317, 327–328, 604/332–335

(56) References Cited

U.S. PATENT DOCUMENTS

| | | | |
|---|---|---|---|
| 2,520,831 A | 8/1950 | Chincholl | 128/283 |
| 3,650,272 A | 3/1972 | Ericson | 128/275 |
| 3,865,165 A | 2/1975 | Glass | 150/1 |
| 4,300,560 A | 11/1981 | Steer et al. | 128/283 |
| 4,306,029 A | 12/1981 | Carpenter | 435/268 |
| 4,449,971 A | 5/1984 | Cawood | 604/54 |
| 4,519,797 A | 5/1985 | Hall | 604/332 |
| 4,521,213 A | 6/1985 | Steigerwald | 604/323 |
| 5,643,236 A | 7/1997 | Hadley | 604/353 |
| 6,045,542 A | * 4/2000 | Cawood | 604/327 |

FOREIGN PATENT DOCUMENTS

| | | |
|---|---|---|
| EP | 0 013 109 | 7/1980 |
| EP | 0 078 930 | 5/1983 |
| EP | 0 147 048 | 7/1985 |
| EP | 0 185 809 | 7/1986 |
| EP | 0 860 154 | 8/1998 |
| GB | 1 128 186 | 9/1968 |
| GB | 2 000 683 | 1/1979 |
| GB | 2 268 065 | 1/1994 |
| GB | 2 295 660 | 6/1996 |
| SE | 313 143 | 8/1969 |
| SE | 443 708 | 3/1986 |
| WO | 93/17642 | 9/1993 |
| WO | 96/19164 | 6/1996 |

* cited by examiner

*Primary Examiner*—Larry I. Schwartz
*Assistant Examiner*—Michele Kidwell
(74) *Attorney, Agent, or Firm*—Jacobson Holman PLLC

(57) ABSTRACT

A collecting bag including a bag member formed by two film blanks with joined edges, and a discharge portion having a discharge opening that is closed by a closure device. The discharge portion has a discharge position, in which the bag is open, and a position of use, in which the bag is closed. At least one open receptacle formed in the bag member accommodates the discharge portion when it is in the position of use of the bag. The open receptacle formed in the bag member has a basis portion in which the film blanks are undetachably connected to each other, and may further include a retaining element in the form of a strip having at least one engagement section for releasable engagement with a corresponding section or corresponding sections on the bag member or on the opposite end of the said retaining element.

19 Claims, 4 Drawing Sheets

COLLECTING BAG HAVING AN ACCOMMODATING MEANS FOR A CLOSURE DEVICE

This is a nationalization of PCT/DK00/00478, filed Sep. 1, 2000 and published in English.

BACKGROUND OF THE INVENTION

1. Field of the Invention

The present invention relates to a collecting bag for human body wastes comprising a bag member formed by two film blanks with joined edges defining the outer contours of the bag member, an inlet opening provided in one of said film blanks, connecting elements surrounding said inlet opening for connection of the bag to a body orifice, a discharge portion at a distance from the inlet opening comprising a discharge opening, a closure device at the discharge portion for bringing the bag from a discharge position, in which the bag is open, to a position of use, in which the bag is closed, and accommodating means for accommodating said closure device in the position of use of the bag.

2. Description of the Related Art

In such collecting bags the discharge portion is normally temporarily attached to the bag member in the position of use of the bag in order to attain a compact appearance in this position and to prevent the discharge portion and the closure device from dangling which might be uncomfortable to the user. In bags having an elongated, substantially flat discharge portion, this portion is folded or rolled up in the direction of the bag member, partly in order to close the bag and partly to attain said compact appearance and the attachment to the bag member.

WO96/19164 discloses a collecting bag of this kind in which the discharge portion is rolled up on a clip fastened to one of the film blanks.

GB patent applications Nos. 2 268 065 and 2 000 683 disclose collecting bags, in which strips of the interlocking-elements type, such as Velcro, are placed on each of the film blanks of the discharge portion and which after rolling or folding the discharge portion tightly are brought into contact with each other.

In EP patent application No. 13 109 the folded discharge portion is tucked into a gap provided between a strip fixed to one wall of the bag and the wall itself.

In all of the above documents it is a prerequisite that the discharge portion is substantially flat. In collecting bags having a closure device of some extent, eg. a valve or a clamp, these solutions may not be applied.

U.S. Pat. No. 2,520,831 discloses a collecting bag in which the folded discharge portion, which is closed by means of a clamp, is accommodated in a pouch provided at the proximal end of the discharge portion in the position of use of the bag, in which the pouch is closed by means of a zipper-like slide fastener. Due to the structure of the elements of the closure device, opening and closing of the bag require some dexterity, eg. the discharge portion has to be held manually within the pouch when activating the slide fastener and has to be withdrawn from the pouch in order to empty the bag. In addition, the use of a slide fastener renders the manufacture of the collecting bag expensive and cumbersome.

U.S. Pat. No. 4,519,797 discloses a cover for an ostomy pouch having a drain fitting at the bottom of the pouch. The cover has an opening allowing the pouch to be mounted in the usual manner on the plate worn by the patient. The cover has an integral pocket which receives the drain fitting to prevent irritation to the sensitive portions of the anatomy.

This solution, however, while preventing the drain fitting from directly contacting sensitive portions of the anatomy, contributes to the bulkiness of the pouch, thereby compromising the demand for discretion.

U.S. Pat. No. 4,449,971 discloses a collecting bag of the initially stated kind, in which the accommodating means in the form of a pocket having an entrance slit is formed on an extension of the bag member. Similar arrangements are shown in e.g. U.S. Pat. Nos 3,865,165 and 4,306,029.

SUMMARY OF THE INVENTION

The object of the present invention is to improve a collecting bag of the kind mentioned in the introduction with respect to ease of operation and manufacturing conditions and which furthermore may be used regardless of the type of closure device, at the same time improving both the comfort and the discretion.

For achieving this, a collecting bag according to the invention is characterized in that said accommodating means comprises at least one open receptacle formed in said bag member within said outer contours and has a basis portion in which said film blanks are undetachably connected to each other, and that the periphery of the basis portion is situated at a distance from the joined edges of the bag member and the discharge portion.

By the provision of an accommodating means in the form of an open receptacle having a basis portion, it is very simple to place the closure device in the accommodating means. The position of the basis portion entails that the outer contours of the bag member are not affected by the accommodating means, and at the same time, a free passage is provided from the bag member to the discharge portion. The undetachable connection between the film blanks makes it possible to lodge the closure device in its entirety in the accommodating means so that it does not protrude outside the arched planes formed by the film blanks when the bag is expanded by the contents. Furthermore, the accommodating means may be formed in an easy and inexpensive manner thus reducing the manufacturing and material costs.

BRIEF DESCRIPTION OF THE DRAWINGS

In the following the invention will be described in further detail with reference to the schematic drawings, in which the bag is shown in the shape it will assume when at least partly filled

DETAILED DESCRIPTION OF THE PREFERRED EMBODIMENTS

Figure 1:
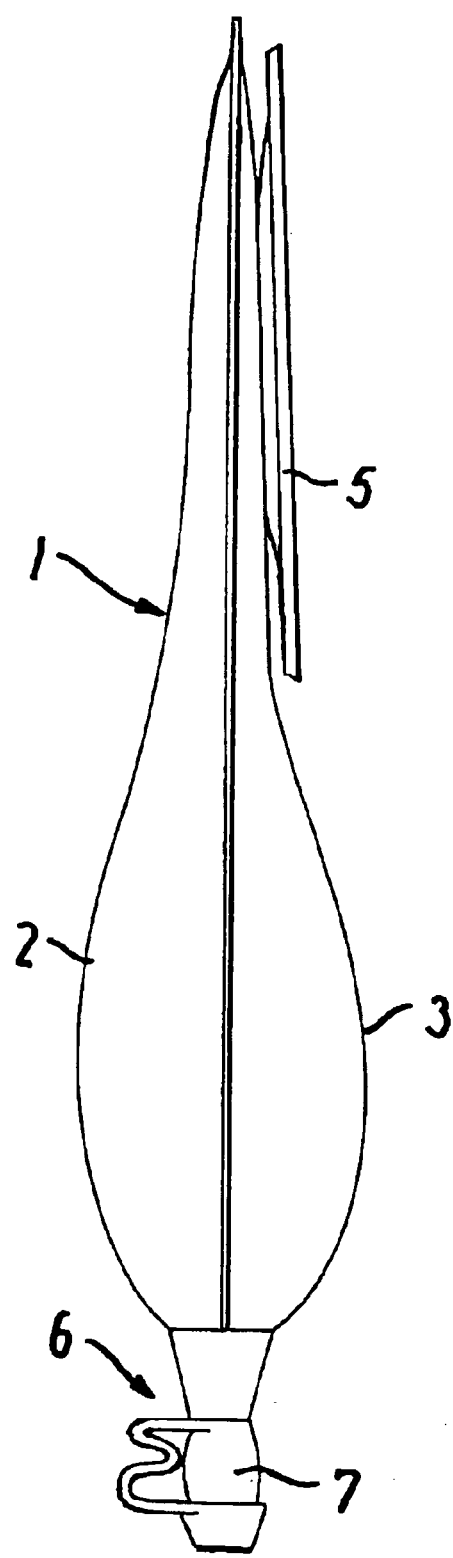
FIG. 1 shows a side view of a collecting bag according to the invention in a discharge position.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The collecting bag shown in the drawings comprises a bag member 1 formed by two film blanks 2,3 which are joined along their edges by means of a seam 4 made by welding or in any other convenient manner and defining the outer contours of the bag member. The film blanks may be made from any suitable flexible plastic sheet or foil material.

In the film blank 3 which in use is intended to face the user and thus forms the back wall of the bag, an inlet opening, not shown, is provided which in a manner known per se is surrounded by connecting elements 5 for connection of the bag to a body orifice in the form of a so-called stoma in the user's abdominal wall.

At a distance from the inlet opening and the connecting elements 5, the bag is designed with a discharge portion 6 having a discharge opening, not shown in detail, through which the bag may be emptied of its contents.

Figure 2:
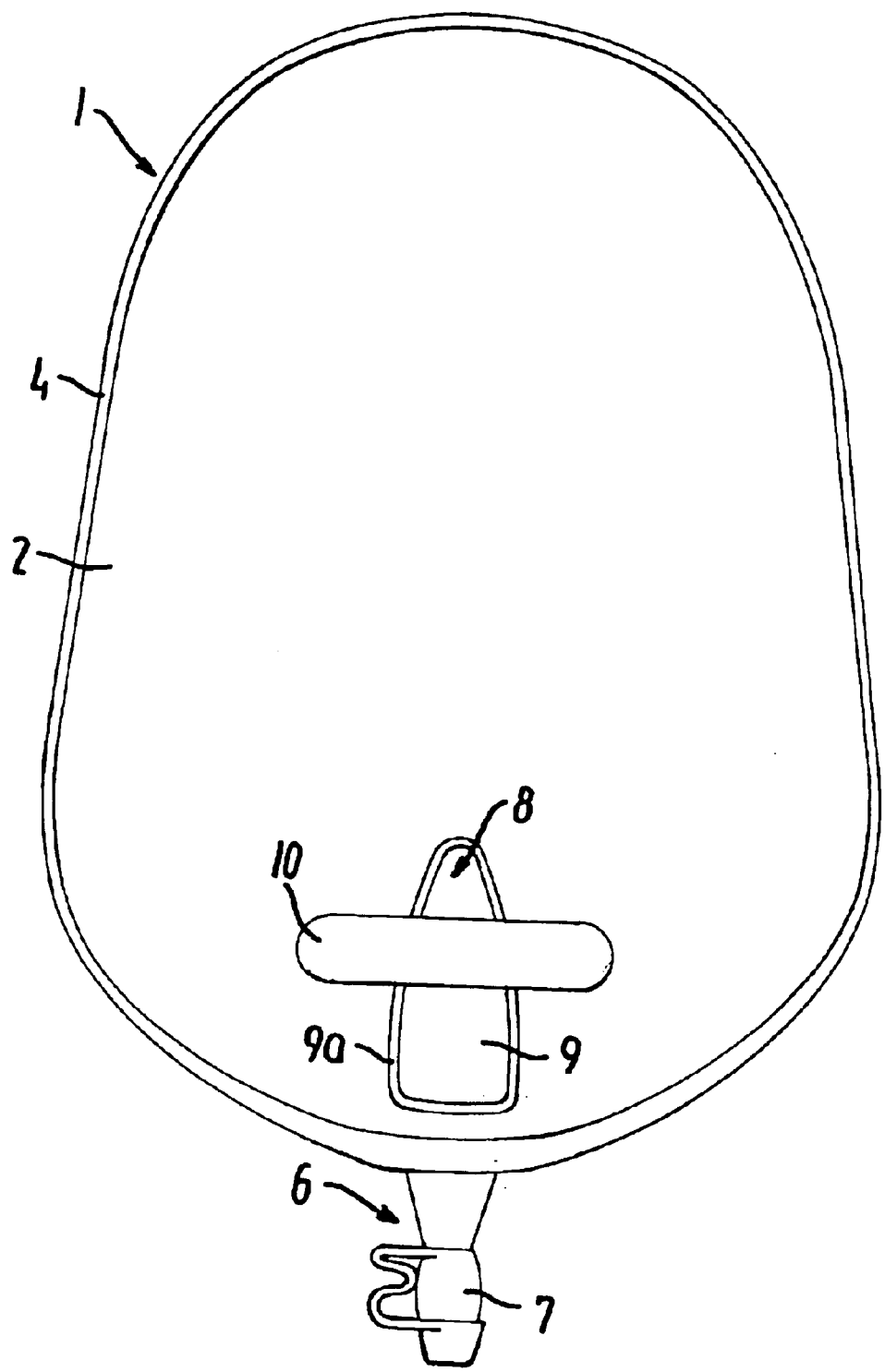
FIG. 2 shows a plan view of the collecting bag shown in FIG. 1.
Figure 3:
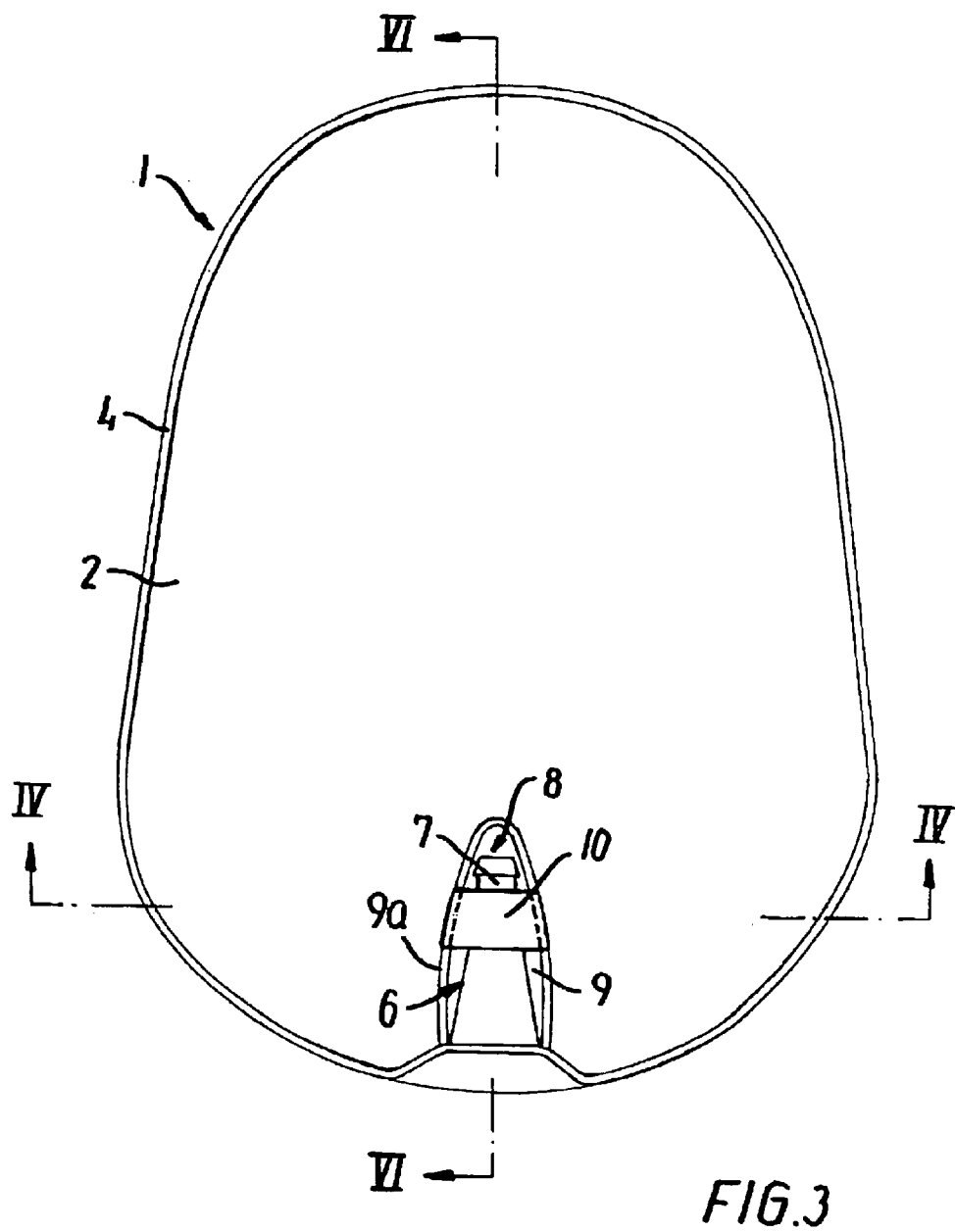
FIG. 3 shows a plan view of the collecting bag in a position of use.
Figure 4:
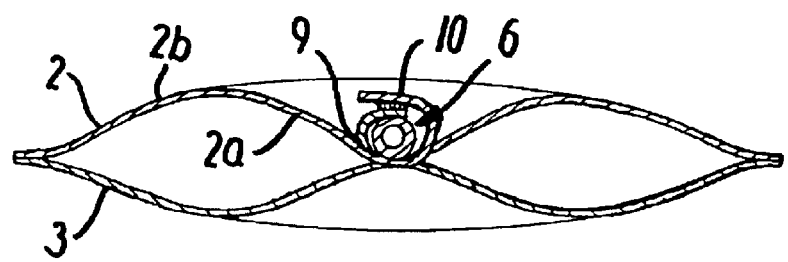
FIG. 4 shows a cross-sectional view of the collecting bag along the line IV—IV in FIG. 3.
Figure 5:
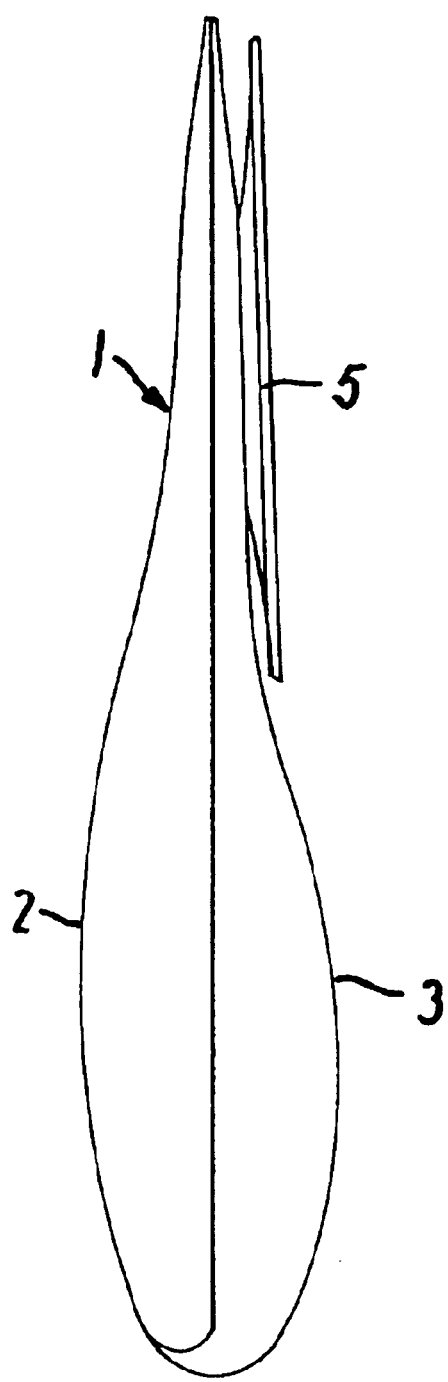
FIG. 5 shows a side view of the collecting bag in the position shown in FIG. 3.
Figure 6:
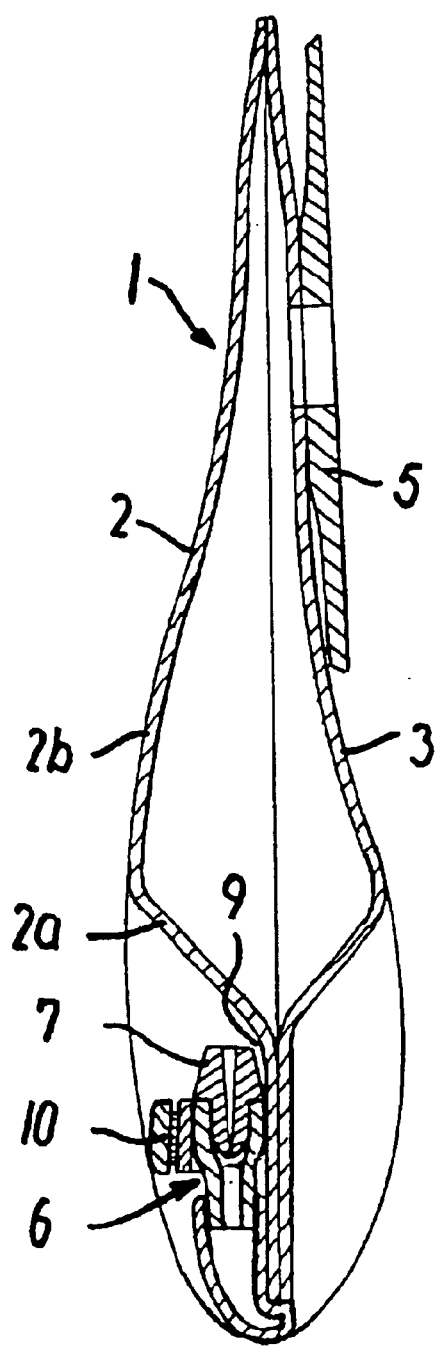
FIG. 6 shows a longitudinal section of the collecting bag along the line VI—VI in FIG. 3.

In order to bring the bag from the open or discharge position shown in FIGS. 1 and 2 to a position of use, in which the bag is closed, the collecting bag comprises a closure device 7 which in the embodiment shown is designed as a valve but which as well be designed in any other way.

An accommodating means 8 for accommodating the closure device 7 in the position of use of the collecting bag is designed in the bag member 1. The accommodating means comprises an open receptacle with a basis portion 9 surrounded by portions 2a of the front film blank 2. In the basis portion 9 the two film blanks 2,3 are, as most clearly seen in FIGS. 4 and 6, connected to each other in an undetachable manner, eg. by means of a welded or heat-sealed joint extending along the periphery 9a of the basis portion 9 or by gluing the film blanks together in this area. As seen in FIGS. 3 to 6 the closure device 7 is accommodated in the accommodating means 8 in its entirety and does not protrude outside the outer contours of the bag in the plane of the bag, neither does it protrude outside the arched plane defined by the remaining portions 2b of the front film, blank. Thus, a very compact appearance of the bag is obtained in the position of use.

It is of course conceivable, although not preferred, to place the closure device in the corresponding receptacle formed at the back of the bag member.

In order to improve the securing of the closure device 7 in the open receptacle formed by the basis portion 9 and the portions 2a of front film blank 2 surrounding the basis portion 9, the accommodating means may further comprise a retaining means, which in the embodiment shown is provided in the shape of a strip 10 which in one end is undetachably connected to the bag member and in the other end has an engagement section for releasable engagement with a corresponding section on the bag member. The engagement sections may comprise interlocking elements, eg. of the Velcro type. The strip 10 may also be undetachably secured in a middle section and have foldable ends with corresponding engagement sections, said foldable ends having lengths enabling them to reach around the closure device 7 for engagement or it may be provided separately and comprise an engagement section in each end.

Other types of retaining means may be conceivable, eg. it is possible to provide the closure device itself with an engagement section for releasable engagement with a corresponding section in the basis portion.

The periphery 9a of the basis portion 9 is situated at a distance from the joined edges of the bag member, ie. the seam 4, and the discharge portion 6 in order to permit the contents of the bag to flow out of the discharge portion 6 and the discharge opening during emptying of the bag. It is of course possible to place the accommodating means in the vicinity of one of the edges as long as there is still a free passage between the bag member and the discharge portion.

The basis portion 9 of the accommodating means has cross-sectional dimensions corresponding to the dimensions of the closure device 7. By this design, a safe retention of the closure device in the accommodating means 8 is obtained and at the same time the volume available for body wastes in the remaining part of the bag is reduced as little as possible.

The invention should not be regarded as being limited to the embodiment described in the above but various modifications may be carried out without departing from the scope of the following claims.

For example, although the invention has been described only with reference to one kind of closure device, viz. a valve, it is of course possible to apply it to other forms of closure devices comprising eg. clamps or adhesive connections.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A collecting bag for human body wastes comprising:
   a bag member formed by two film blanks having joined edges defining tie outer contours of the bag member,
   an inlet opening provided in one of said film blanks, connecting elements surrounding said inlet opening for connection of the bag around a body orifice;
   a discharge portion at a distance from the inlet opening and including a discharge opening;
   a closure device at the discharge portion 6 for closing said discharge opening, said discharge portion having a discharge position, in which the bag is open, and a position of use, in which the bag is closed; and
   accommodating means for accommodating said closure device in the position of use of the bag,
   said accommodating means having at least one open receptacle formed in said bag member within said outer contours, and a basis portion in which said film blanks are undetachably connected to each other, a periphery of the basis portion is being situated at a distance from the joined edges of the bag member and the discharge portion and, when said discharge portion is in said position of use, said closure device overlying said basis portion and fitting within said open receptacle.

2. The collecting bag according to claim 1, wherein said film blanks are connected to each other by a heat-sealed joint extending along the periphery of the basis portion.

3. The collecting bag according to claim 1, wherein said film blanks are connected to each other by gluing.

4. The collecting bag according to claim 1, wherein said accommodating means includes a retaining element for holding the closure device in said open receptacle in the position of use of the bag.

5. The collecting bag according to claim 4, wherein said retaining element comprises a strip having at least one engagement section for releasable engagement with a corresponding section or corresponding sections on said bag member or on the opposite end of said retaining element.

6. The collecting bag according to claim 1, wherein said basis portion has cross-sectional dimensions corresponding to the dimensions of the closure device.

7. A collecting bag for human body wastes comprising:

a bag member formed by first and second film blanks having joined edges defining outer contours of the bag member;

an inlet opening provided in one of said film blanks for communication with a body orifice;

a discharge component at a distance from the inlet opening and including a discharge opening and a closure device for closing said discharge opening, said discharge component having a discharge position and an in-use position; and an open recessed area formed in said bag member by a basis portion, in which said film blanks are undetachably connected to each other, and portions of the first film blank surrounding said basis portion, said recessed area being adjacent said discharge component and fully accommodating said closure device in the in-use position so that said closure device does not protrude outside an arched plane defined by remaining portions of said first film blank.

8. The collecting bag according to claim 7, wherein a periphery of the basis portion is situated at a distance from the joined edges of the bag member and the discharge component.

9. The collecting bag according to claim 8, wherein said film blanks are connected to each other by a heat-sealed joint extending along the periphery of the basis portion.

10. The collecting bag according to claim 7, wherein said closure device is moved toward said inlet opening and overlies said basis portion when said discharge component is in said in-use position.

11. The collecting bag according to claim 7, wherein said film blanks are connected to each other by gluing.

12. The collecting bag according to claim 7, further comprising a retaining element for holding the closure device in said open recessed area in the in-use position.

13. The collecting bag according to claim 12, wherein said retaining element includes a strip having at least one engagement section for releasable engagement with a corresponding section or corresponding sections on said bag member or on the opposite end of said retaining element.

14. The collecting bag according to claim 7, wherein said basis portion has cross-sectional dimensions corresponding to dimensions of the closure device.

15. A collecting bag for human body wastes comprising:

a bag member formed by first and second film blanks having joined edges defining outer contours of the bag member;

an inlet opening provided in one of said film blanks for connection of the bag around a body orifice;

an elongated discharge portion extending from said bag member at a distance from the inlet opening and including a discharge opening adjacent a distal end of said discharge portion;

a closure device at the distal end of said discharge portion for closing said discharge opening; and an open recessed area in said bag member adjacent a proximal end of said discharge portion, said open receptacle formed by a basis portion, in which said film blanks are undetachably connected to each other, and inwardly directed portions of the first film blank surrounding said basis portion;

said bag having a discharge position in which said discharge portion and closure device extend outwardly from said bag member for emptying said bag, and an in-use position, in which said discharge portion is folded toward said inlet opening so that said closure device is fully accommodated within said open recessed area and does not protrude beyond an arched plane defined by remaining portions of said first film blank.

16. The collecting bag according to claim 15, wherein a periphery of the basis portion is situated at a distance from the joined edges of the bag member and the discharge portion.

17. The collecting bag according to claim 15, further comprising a retaining element for holding the closure device in said open recessed area in the in-use position.

18. The collecting bag according to claim 17, wherein said retaining element includes a strip having at least one engagement section for releasable engagement with a corresponding section or corresponding sections on said bag member or on the opposite end of said retaining element.

19. The collecting bag according to claim 15, wherein said basis portion has cross-sectional dimensions corresponding to dimensions of the closure device.

\* \* \* \* \*